United States Patent
Herold et al.

(10) Patent No.: US 9,757,488 B2
(45) Date of Patent: Sep. 12, 2017

(54) METHOD AND DEVICE FOR STERILISING AND DEVICE FOR BLOW-MOULDING CONTAINERS

(75) Inventors: Thomas Herold, Ahrensburg (DE); Harald Rieger, Hamburg (DE); Dieter Klatt, Hamburg (DE); Martin Gerhards, Hamburg (DE)

(73) Assignee: KHS Corpoplast GmbH, Hamburg (DE)

( * ) Notice: Subject to any disclaimer, the term of this patent is extended or adjusted under 35 U.S.C. 154(b) by 745 days.

(21) Appl. No.: 14/123,687

(22) PCT Filed: Jun. 1, 2012

(86) PCT No.: PCT/EP2012/002325
§ 371 (c)(1),
(2), (4) Date: Dec. 3, 2013

(87) PCT Pub. No.: WO2012/167890
PCT Pub. Date: Dec. 13, 2012

(65) Prior Publication Data
US 2014/0119988 A1 May 1, 2014

(30) Foreign Application Priority Data
Jun. 6, 2011 (DE) .......... 10 2011 104 024

(51) Int. Cl.
*B29C 49/42* (2006.01)
*A61L 2/16* (2006.01)
(Continued)

(52) U.S. Cl.
CPC .............. *A61L 2/16* (2013.01); *A61L 2/208* (2013.01); *A61L 2/26* (2013.01); *B29C 49/4252* (2013.01); *A61L 2202/23* (2013.01)

(58) Field of Classification Search
CPC ........ B29C 49/4252; B29C 2049/4635; B29C 2049/4679; B29C 2049/4682;
(Continued)

(56) References Cited

U.S. PATENT DOCUMENTS 3,712,784 A * 1/1973 Siard .......................... A61L 2/04
134/166 R
4,432,720 A * 2/1984 Wiatt ...................... B29C 49/28
425/534
(Continued)

FOREIGN PATENT DOCUMENTS

| CN | 1602247 A | 3/2005 |
|---|---|---|
| CN | 101987696 A | 3/2011 |

(Continued)

OTHER PUBLICATIONS

WO 2011141011 with English Machine Translation.*
(Continued)

*Primary Examiner* — Alison L Hindenlang
*Assistant Examiner* — Jerzi H Moreno Hernandez
(74) *Attorney, Agent, or Firm* — Rankin, Hill & Clark LLP (57) ABSTRACT

The present invention relates to a method and device for sterilizing parisons made of a thermoplastic material that are intended for producing blow-molded containers. During the sterilizing process a sterilizing agent is introduced into an interior of the parison by an applicator. At least one gas is supplied to the applicator via at least one supply element, at least sections of which are arranged in a horizontal direction next to a transport path of the applicator. The supply element comprises at least one outlet opening facing towards the applicator. At least one pressure-applying element is
(Continued)

arranged between the applicator and the supply element and is resiliently clamped between the applicator and the supply element.

13 Claims, 10 Drawing Sheets

(51) Int. Cl.
   *A61L 2/26* (2006.01)
   *A61L 2/20* (2006.01)
(58) Field of Classification Search
   CPC .. B29C 2791/005; A61L 2/26; A61L 2202/23; A61L 2/16; A61L 2/208; B67C 3/2642; B67C 3/26; B67C 7/0073; B67C 7/0086; B08B 9/426; B08B 9/423; B08B 9/32; B08B 9/30; B29L 2031/7158
   See application file for complete search history.

(56) References Cited

U.S. PATENT DOCUMENTS

| 5,641,451 A * | 6/1997 | Orimoto | B29C 49/421 264/521 |
|---|---|---|---|
| 2009/0081326 A1 | 3/2009 | Adriansens et al. | |
| 2011/0061343 A1 * | 3/2011 | Roithmeier | B29C 49/42 53/452 |
| 2011/0272861 A1 * | 11/2011 | Humele | A61L 2/12 264/457 |

FOREIGN PATENT DOCUMENTS

| DE | 2352926 A1 | 4/1975 |
|---|---|---|
| DE | 4212583 A1 | 10/1993 |
| DE | 4340291 A1 | 6/1995 |
| DE | 19906438 A1 | 8/2000 |
| DE | 69900390 T2 | 6/2002 |
| DE | 102007050582 A1 | 4/2009 |
| DE | 102008056346 A1 | 5/2010 |
| DE | 102009041215 A1 | 3/2011 |
| DE | 102010020996 A1 | 11/2011 |
| DE | 102010026166 A1 | 1/2012 |
| EP | 0996530 B1 | 1/2003 |
| EP | 2138298 A2 | 12/2009 |
| EP | 2295324 A1 | 3/2011 |
| WO | 99/51497 A1 | 10/1999 |
| WO | 2006/136499 A1 | 12/2006 |
| WO | 2009052800 A1 | 4/2009 |
| WO | 2010/020530 A1 | 2/2010 |
| WO | 2010/052068 A1 | 5/2010 |
| WO | 2011/141011 A1 | 11/2011 |
| WO | 2012/000486 A1 | 1/2012 |

OTHER PUBLICATIONS

English Translation of the International Preliminary Report on Patentability dated Dec. 10, 2013, in corresponding International Application No. PCT/EP2012/002325, filed Jun. 1, 2012.

* cited by examiner

METHOD AND DEVICE FOR STERILISING AND DEVICE FOR BLOW-MOULDING CONTAINERS

BACKGROUND OF INVENTION

Field of Invention

The invention relates to a method for sterilizing parisons consisting of a thermoplastic material that are provided for the manufacture of blow-molded containers in which a sterilization agent is introduced by an applicator into an inner space of the parison.

Furthermore, the invention relates to a device for sterilizing parisons consisting of a thermoplastic material that are provided for the manufacture of blow-molded containers, whereby a supply device for loading an inner space of the parison with a sterilization agent comprises at least one applicator that can be transported at least in sections together with the parison.

The invention also relates to a method for the blow-molding of containers that comprises at least one blow station, arranged on a carrier structure, for transforming thermoplastic parisons into the containers, whereby a sterilization device is arranged in a transport direction of the parisons in front of the blow station.

Brief Description of Related Art

A manufacture of sterile, blow-molded containers typically takes place in such a manner that these containers are sterilized using hydrogen peroxide or other chemicals after their blow-molding and before being filled. The sterilization of the parisons used in the blow-molding of the containers as finished product, in particular the area of the inner surface of these parisons, is also known.

In a container molding by the action of blowing pressure, parisons consisting of a thermoplastic material, for example, parisons consisting of PET (polyethylene terephthalate) are supplied inside a blow-molding machine to different processing stations. Such a blow-molding machine typically comprises a heating device as well as a blowing device in whose range the previously tempered parison is expanded by biaxial orientation to a container. The expansion takes place with compressed air that is introduced into the parison to be expanded. The technical course of the method in such an expansion of the parison is explained in DE-OS 43 40 291.

The basic construction of a blow station for the container molding is described in DE-OS 42 12 583. Possibilities for tempering the parisons are explained in DE-OS 23 52 926.

Inside the device for the blow-molding the parisons and the blown containers can be transported with the aid of various handling devices. In particular, the use of transport mandrels onto which the parisons are mounted has proven itself. However, the parisons can also be handled with other carrying devices. The use of gripping devices for handling parisons and the use of spreading mandrels that can be introduced into a mouth area of the parison for holding it also belong to the available constructions.

A handling of containers using transfer wheels is described, for example, in DE-OS 199 06 438 in an arrangement of the transfer wheel between a blow wheel and output section.

The already explained handling of the parisons takes place on the one hand in the so-called two-stage methods in which the parisons are at first produced in an injection-molding method, subsequently intermediately stored and only later conditioned as regards their temperature and inflated to a container. On the other hand, there is a usage in the so-called one-stage methods in which the parisons are suitably tempered immediately after their injection-molding manufacture and a sufficient solidification and subsequently inflated.

As regards the blow stations used, various embodiments are known. In blow stations arranged on rotating transport wheels a book-like ability of the mold carriers to fold out is frequently found. However, it is also possible to use mold carriers that can shift relative to each other or that are guided in a different manner. In the case of stationary blow stations, that are in particular suited for receiving several cavities for container molding, plates typically arranged parallel to each other are used as mold carriers.

As regards the sterilization of parisons, various methods and devices are already known from the prior art that, however, all exhibit disadvantages specific to their methods and that oppose a reliable sterilization of the parisons at high throughput rates at the same time.

For example, in EP-A 1 086 019 the sterilization of hot parisons with a hot, gaseous sterilization agent is described. Separate treatment stations arranged in sequence are used, namely, a first heating module, a sterilization module and a second heating module. The disadvantage here is the temperature behavior of the parison during the sterilization procedure and the uncontrolled exiting of the sterilization agent from the parison during the heating.

EP-A 1 896 245 describes a method in which prior to the heating a gaseous sterilization agent is introduced into a cold parison and condensed there. The ensuring of a complete formation of condensate on the entire inside surface of the parison is problematic here since the incoming, hot sterilization agent raises the temperature of the inner wall of the parison. Furthermore, the sterilization agent also exits from the parison here after its evaporation in the area of the heating in an uncontrolled manner during the heating.

EP-A 2 138 298 describes a device in which the sterilization devices are arranged by way of precaution in front of the blowing module used as well as behind the blowing module used. This results in a very great expense for machine construction.

WO 2010/020530 A1 describes the arrangement of a sterilization device between a heating device and the blowing module. In this method the charged amount of sterilization agent into the area of the blowing module can be predicted only with difficulty. Moreover, the amount of sterilization agent discharged into the environment cannot be controlled and a corresponding contamination is not excluded.

In general the attempt is made to avoid an uncontrolled propagation of the sterilization agent in the heating area as well as in the area of the blowing module since the sterilization agents used frequently have corroding properties. Thus, the greater a discharged amount of sterilization agent is, the higher the expense for machine construction for avoiding corrosion damage, for example, by the use of especially corrosion-resistant materials that are therefore more expensive.

On the other hand, the attempt is made to carry out the sterilization in the shortest possible process time and to minimize the expense for the machine construction for constructively realizing the sterilization device.

The present invention has the problem of improving a method of the initially cited type in such a manner that a reliable sterilization can be carried out in a simple manner.

BRIEF SUMMARY OF THE INVENTION

This problem is solved in accordance with the invention in that at least one gas is supplied to the applicator via at least one supply element that is arranged at least in areas in a horizontal direction adjacent to a transport path of the applicator and comprises at least one discharge opening facing the applicator, and that at least one press-on element is arranged between the applicator and the supply element which element is resiliently tensioned between the applicator and the supply element.

Another problem of the present invention is to construct a device of the initially cited type in such a manner that an effective sterilization can be carried out with low expense.

This problem is solved in accordance with the invention in that a supply element for supplying the sterilization agent is arranged at least in areas in a horizontal direction adjacent to a transport path of the applicator and has at least one discharge opening facing the applicator, and that at least one press-on element is arranged between the applicator and the supply element which press-on element can be resiliently tensioned between the applicator and the supply element.

The combination of the applicator, the supply element and of the press-on element that can be tensioned makes possible a sealed-off supply and/or discharge of the sterilization agent to the parisons to be sterilized with a simple construction at the same time. In particular, it is possible to design the movement courses to be carried out to be continuous, thus supporting a high throughput amount. As a result of the resilient tensioning of the press-on element between the applicator and the supply element, the required seal is made available.

This supports a mechanically simple construction in that the press-on element is moved together with the applicator.

In order to reduce an occurring wear, it was also provided that the applicator is moved past the press-on element.

A compact embodiment is supported in that the applicator is constructed as part of a carrier element for the parisons.

Undesired discharge amounts of the sterilization agent can furthermore be reduced in that at least two applicators are sealed off relative to one another.

In particular, it was provided that the sealing is constructed as a circumferential seal. The seal preferably consists of an elastomer.

A modular construction is supported by the fact that the press-on element is resiliently supported on the applicator.

The number of press-on elements can be reduced in that the press-on element is resiliently supported on the supply element.

It was provided, for example, in the case of a movable construction of the supply element that the supply element comprises discharge elements arranged on a rotating wheel.

According to another embodiment it is also possible that the supply element comprises discharge elements arranged on a revolving chain.

An optimal utilization of a movement range can take place in that the discharge element is guided at least in sections parallel to a direction of movement of the applicator.

A typical use is defined in that a blow-molding machine for transforming the parisons into containers is provided in the area of its heating section with the sterilization device.

BRIEF DESCRIPTION OF THE DRAWINGS

Exemplary embodiments of the invention are schematically shown in the drawings. In the drawings.

DETAILED DESCRIPTION OF THE INVENTION

In the following at first the basic construction of a blow-molding machine will be described before an explanation of the detailed construction of the device for sterilizing the parisons (1) by using a sterilization agent and before an explanation of a concrete insertion of a corresponding device into a blow-molding machine.

Figure 1:
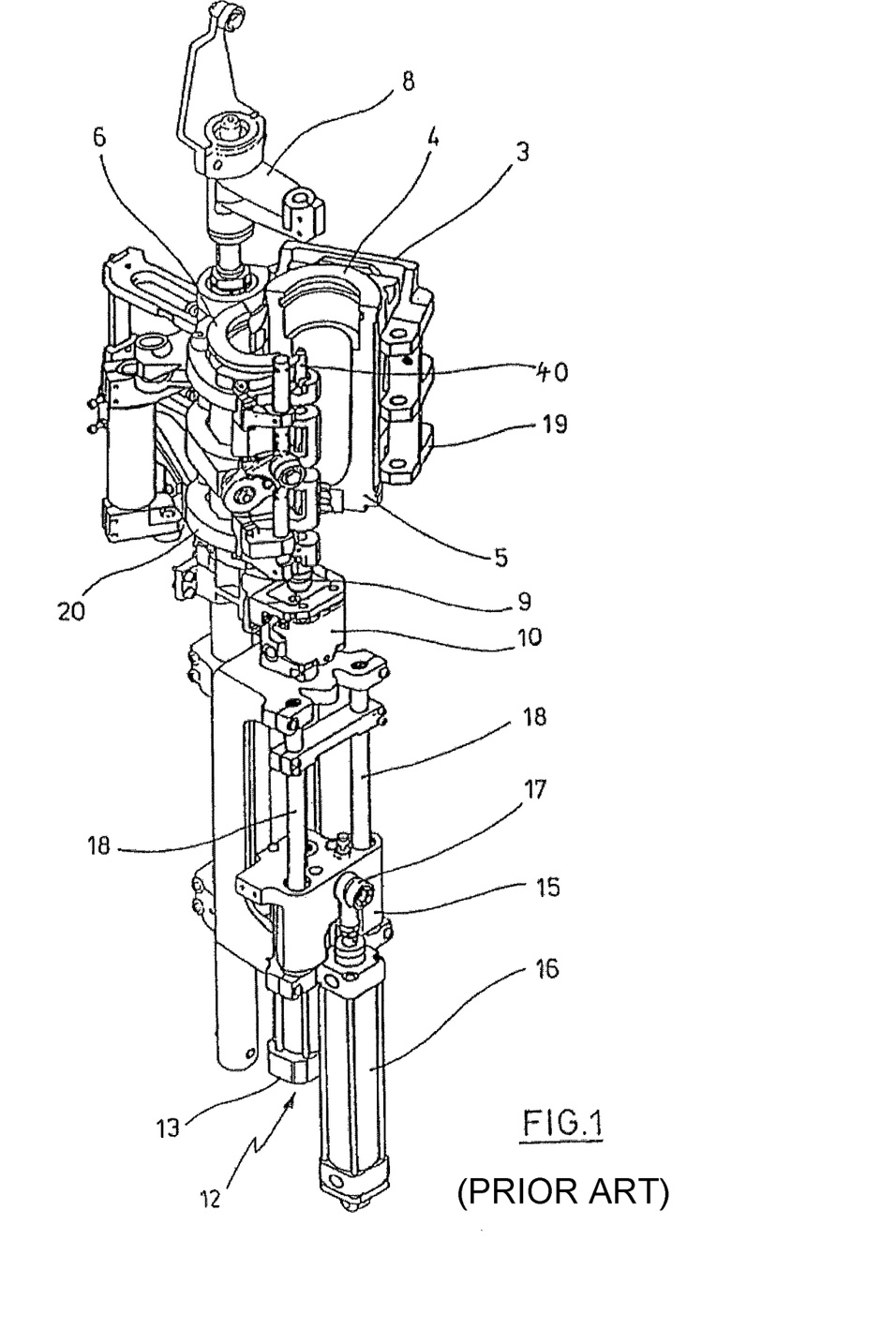
FIG. 1 shows a perspective view of a blow station for producing containers from parisons.
Figure 2:
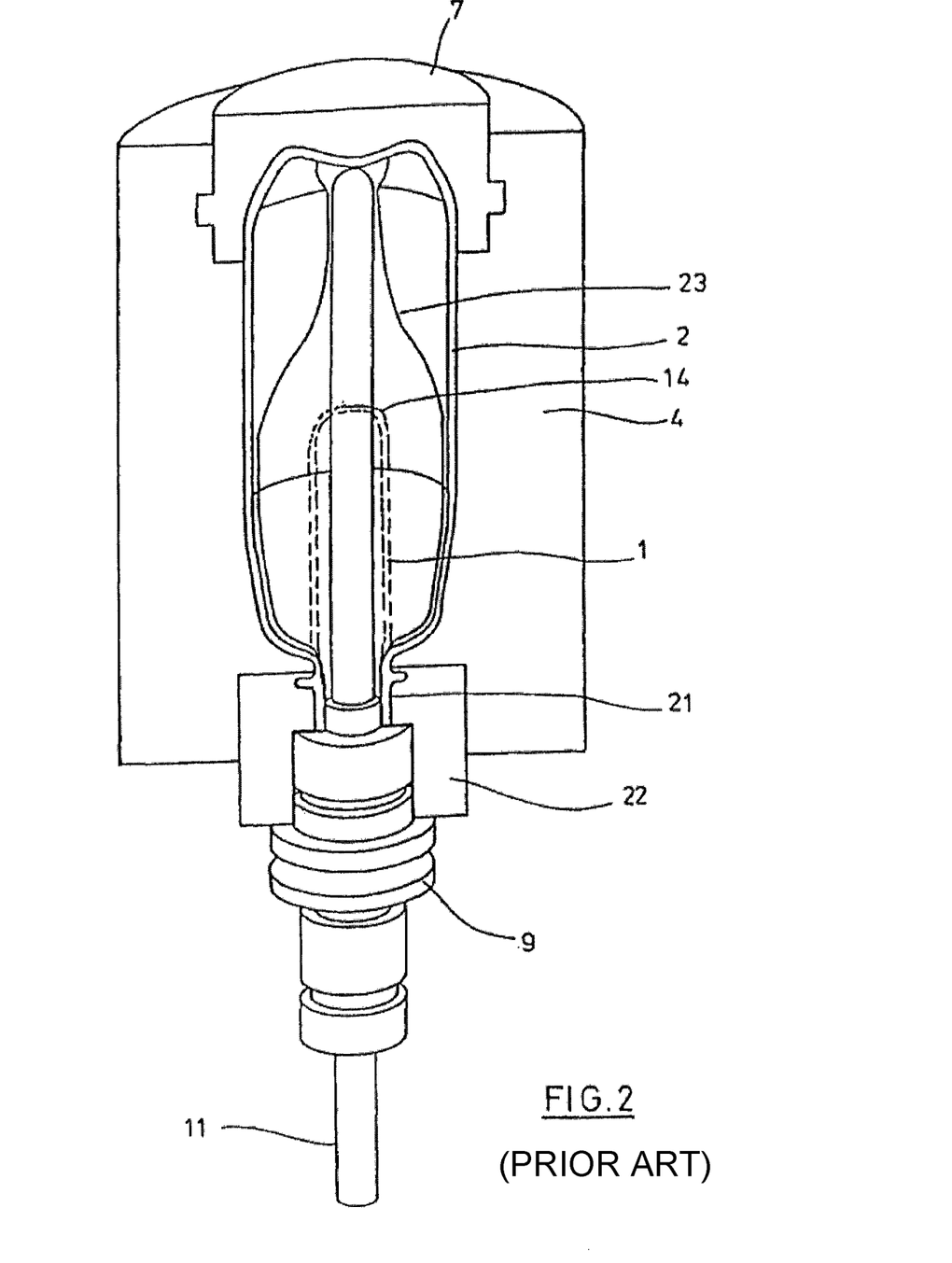
FIG. 2 shows a longitudinal section through a blow mold in which a parison is stretched and expanded.

The basic construction of a device for transforming parisons (1) into containers (2) is shown in FIG. 1 and in FIG. 2.

The device for molding the container (2) consists substantially of a blowing station (3) that is provided with a blow mold (4) into which a parison (1) can be inserted. The parison (1) can be an injection-molded part consisting of polyethylene terephthalate. In order to make it possible to insert the parison (1) into the blow form (4) and to make it possible to remove the finished container (2), the blow form (4) consists of mold parts (5, 6) and a bottom part (7) that can be positioned by a lifting device (8). The parison (1) can be held in the area of the blow station (3) by a transport mandrel (9) that passes together with the parison (1) through a plurality of treatment stations inside the device. However, it is also possible to insert the parison (1), for example, by grippers or other handling elements directly into the blow mold (4).

In order to make possible a compressed air supply line a connection piston (10) is arranged underneath the transport mandrel (9) which piston supplies compressed air to the parison (1) and at the same time makes a seal relative to the transport mandrel (9). However, in a modified construction it is basically also conceivable to use fixed compressed air supply lines.

A stretching of the parison (1) takes place with the aid of a stretching rod (11) positioned by a cylinder (12). However, it is also conceivable to perform a mechanical positioning of the stretching rod (11) by cam segments loaded by tap rollers. The use of cam segments is in particular advantageous if a plurality of blow stations (3) are arranged on a rotating blow wheel. A use of cylinders (12) is advantageous if stationarily arranged blow stations (3) are provided.

In the embodiment shown in FIG. 1 the stretching system is constructed in such a manner that a tandem arrangement of two cylinders (12) is made available. At first, the stretching rod (11) is moved by a primary cylinder (13) before the start of the actual stretching process into the area of a bottom (14) of the parison (1). During the actual stretching process the primary cylinder (13) is positioned with extended stretching rod together with a carriage (15) carrying the primary cylinder (13) by a secondary cylinder (16) or via a cam control. It was provided in particular that the secondary cylinder (16) is inserted by cam control in such a manner that a current stretching position is given by a guide roller (17) that slides along a curved path during the execution of the stretching process. The guide roller (17) is pressed by the secondary cylinder (16) against the guide track. The carriage (15) slides along two guide elements (18).

After a closing of the mold parts (5, 6) arranged in the area of carriers (19, 20) a locking of the carriers (19, 20) relative to one another takes place with the aid of a locking device (40).

In order to adapt to different forms of a mouth section (21) of the parison (1), the use of separate threaded inserts (22) is provided in the area of the blow mold (4) in accordance with FIG. 2.

FIG. 2 also shows, sketched in dotted lines, the parison (1) and schematically a developing container bubble (23) in addition to the blown container (2).

Figure 3:
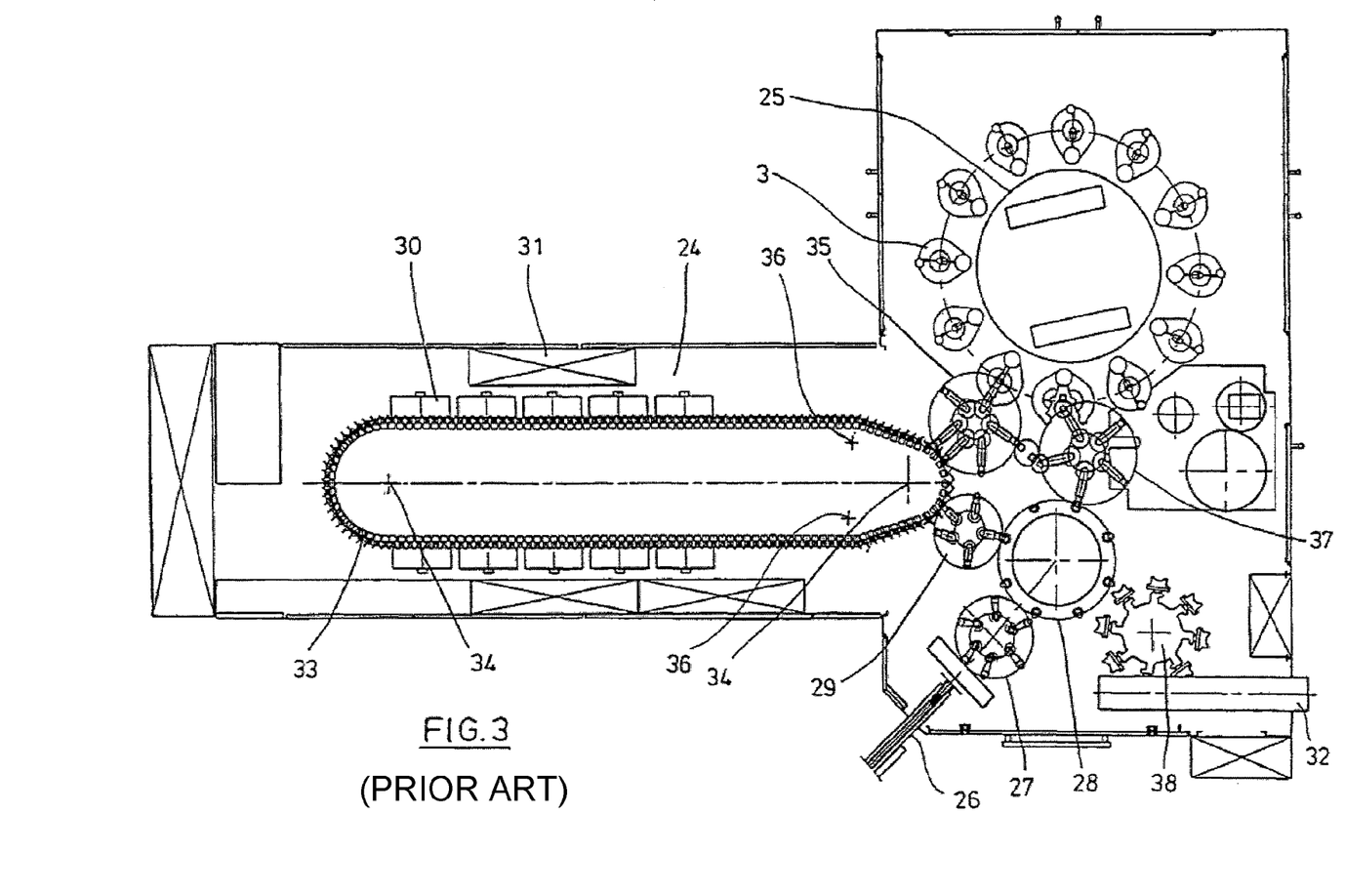
FIG. 3 shows a sketch for illustrating a basic construction of a device for the blow-molding of containers.

FIG. 3 shows the basic construction of a blow-molding machine provided with a heating section (24) as well as a rotating blow wheel (25). Starting from a parison insertion (26) the parisons (1) are transported by transfer wheels (27, 28, 29) into the area of the heating section (24). Heating radiators (30) as well as blowers (31) are arranged along the heating section (24) in order to temper the parisons (1). After a sufficient tempering of the parisons (1) they are transferred onto the blow wheel (25), in whose range the blow stations (3) are arranged. The containers (2) that are finished being blown are supplied by other transfer wheels to an output section (32).

In order to be able to transform a parison (1) into a container (2) in such a manner that the container (2) has material properties that ensure the ability to be used for a long time for food, in particular beverages, filled inside the container (2), special method steps must be maintained during the heating and orienting of the parisons (1). In addition, advantageous effects can be achieved by maintaining special dimensioning regulations.

Various plastics can be used as thermoplastic material. For example, PET, PEN or PP are capable of being used.

The expansion of the parison (1) during the orientation procedure takes place by the supplying of compressed air. The supplying of compressed air is into a pre-blowing phase in which gas, for example, compressed air, is supplied at a low pressure level and is subdivided into a following main blowing phase in which gas is supplied with a higher pressure level. During the pre-blowing phase compressed air is typically used with a pressure in the interval of 10 bar to 25 bar and during the main blowing phase compressed air is supplied with a pressure in the interval from 25 bar to 40 bar.

It can also be recognized from FIG. 3 that in the embodiment shown the heating section (24) is formed from a plurality of rotating transport elements (33) that are lined up adjacent to each other in a chain-like manner and are guided along by deflection wheels (34). In particular, it is provided that a substantially rectangular basic contour is set by the chain-like arrangement. In the embodiment shown an individual deflection wheel (34) with relatively large dimensions in the area of the extension of the heating section (24) facing the transfer wheel (29) and facing an input wheel (35), and in the area of adjacent deflections two deflection wheels (36) with comparatively smaller dimensions are used. Basically, however, any other guides are conceivable.

In order to make possible the tightest possible arrangement of the transfer wheel (29) and of the input wheel (35) relative to each other, the arrangement shown proves to be especially advantageous since three deflection wheels (34, 36) are positioned in the area of the corresponding extension of the heating section (24) and the smaller deflection wheels (36) are in the area of the transfer to the linear courses of the heating section (24) and the larger deflection wheel (34) is in the immediate transfer arranged to the transfer wheel (29) and to the input wheel (35). It is also possible, for example, to use a rotating heating wheel as an alternative to using chain-like transport elements (33).

After a finished blowing of the containers (2), they are guided by a removal wheel (37) out of the area of the blow stations (3) and transported via the transfer wheel (28) and a discharge wheel (38) to the output section (32).

Figure 4:
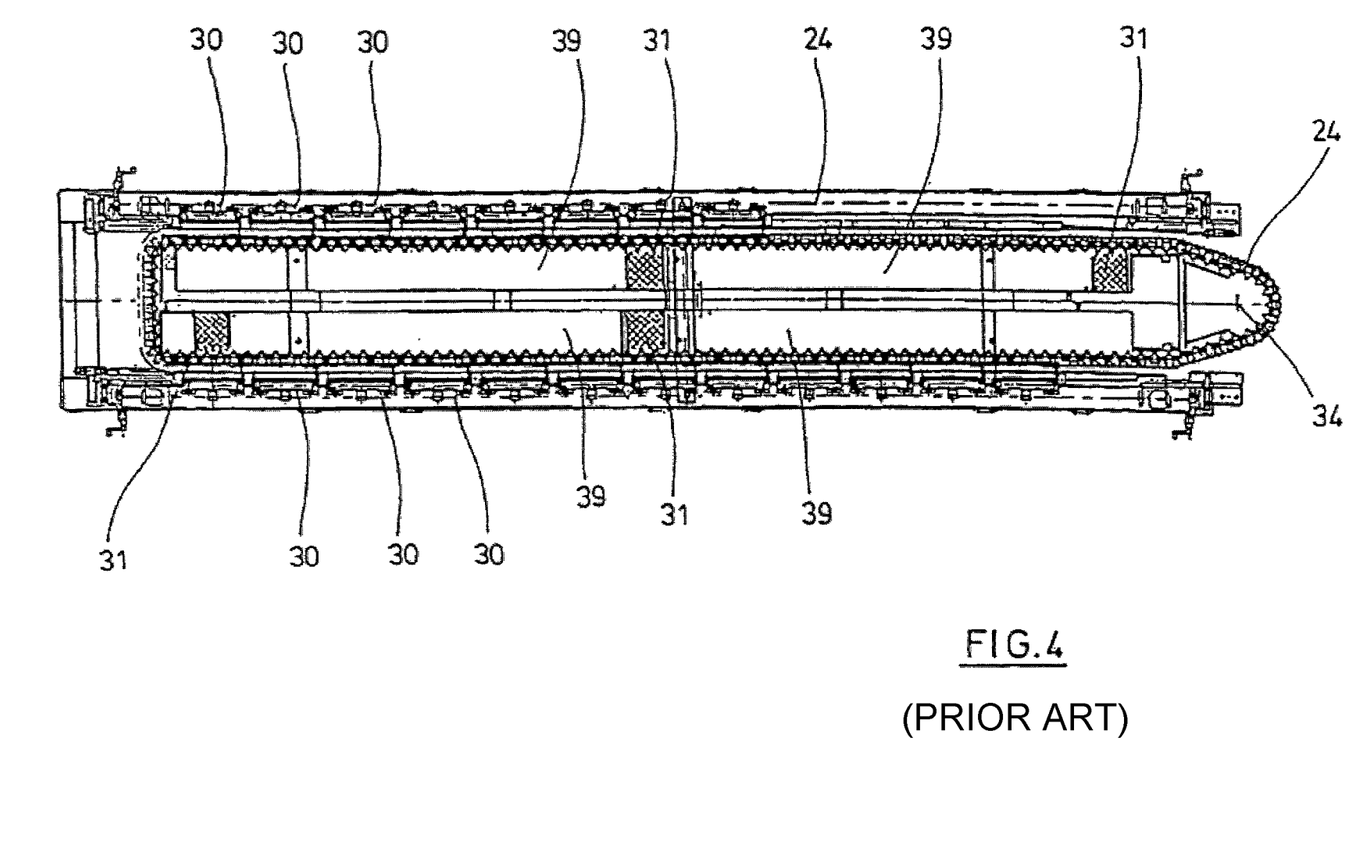
FIG. 4 shows a modified heating section with enlarged heating capacity.

In the modified heating section (24) shown in FIG. 4 a greater amount of parisons (1) per time unit can be tempered by the greater number of heating radiators (30). The blowers (31) conduct cooling air here into the area of cooling air conduits (39) that are located opposite the associated heating radiators (30) and emit the cooling air via outflow openings. The arrangement of the outflow directions realizes a flow direction for the cooling air substantially transversely to a transport direction of the parisons (1). The cooling air conduits (39) can make reflectors for the heating radiation available in the area of surfaces opposite the heating radiators (30). It is also possible to also realize a cooling of the heating radiators (30) via the discharged cooling air.

Figure 5:
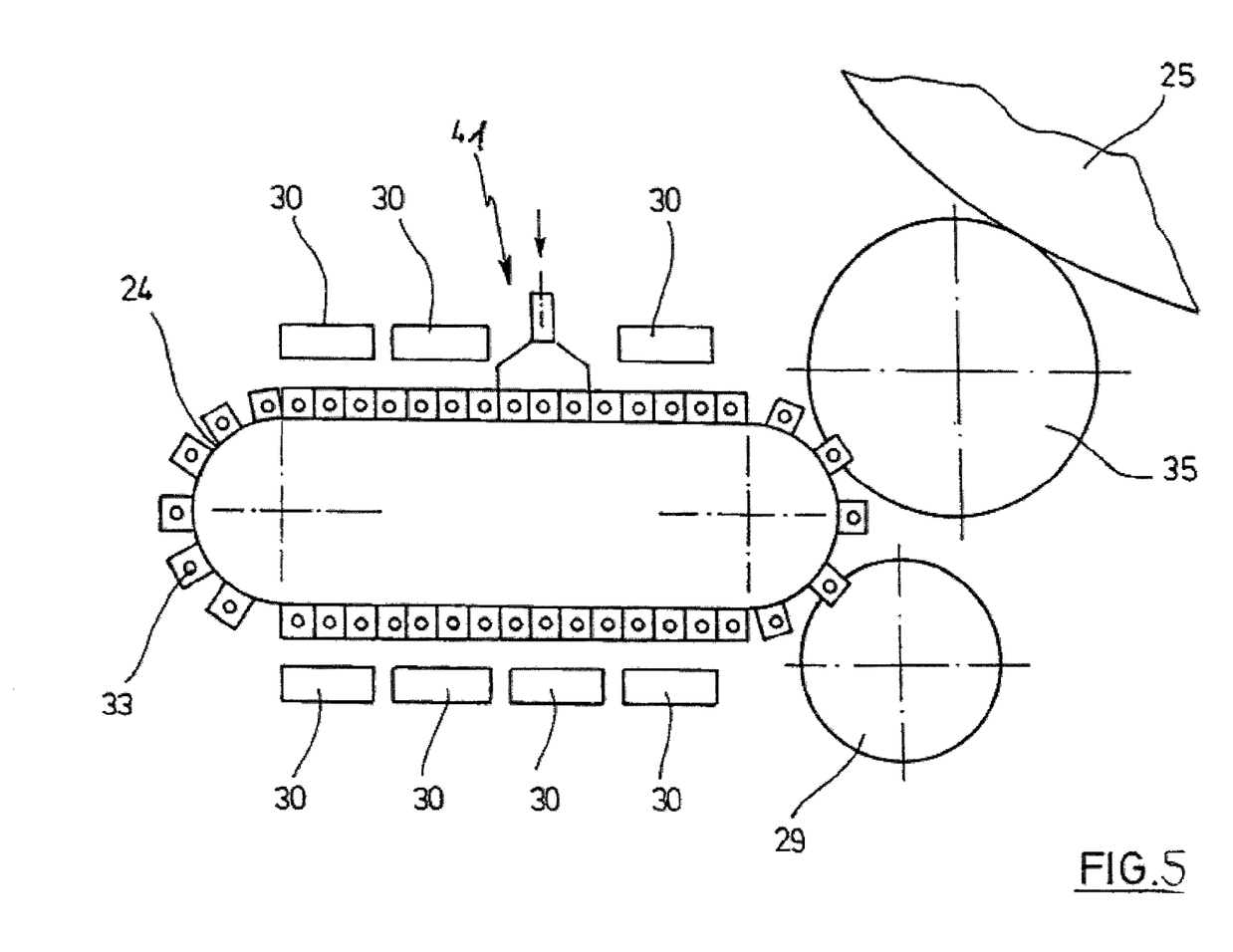
FIG. 5 shows a schematic view of a heating module of a blow-molding machine in which a sterilization device is arranged in the area of the heating module.

FIG. 5 schematically shows in a greatly simplified manner an arrangement similar to the presentation in FIG. 3 with the additional arrangement of a sterilization device (41) in the area of the heating section (24). The transport elements (33) of the heating section (24) are additionally sketched in.

Figure 6:
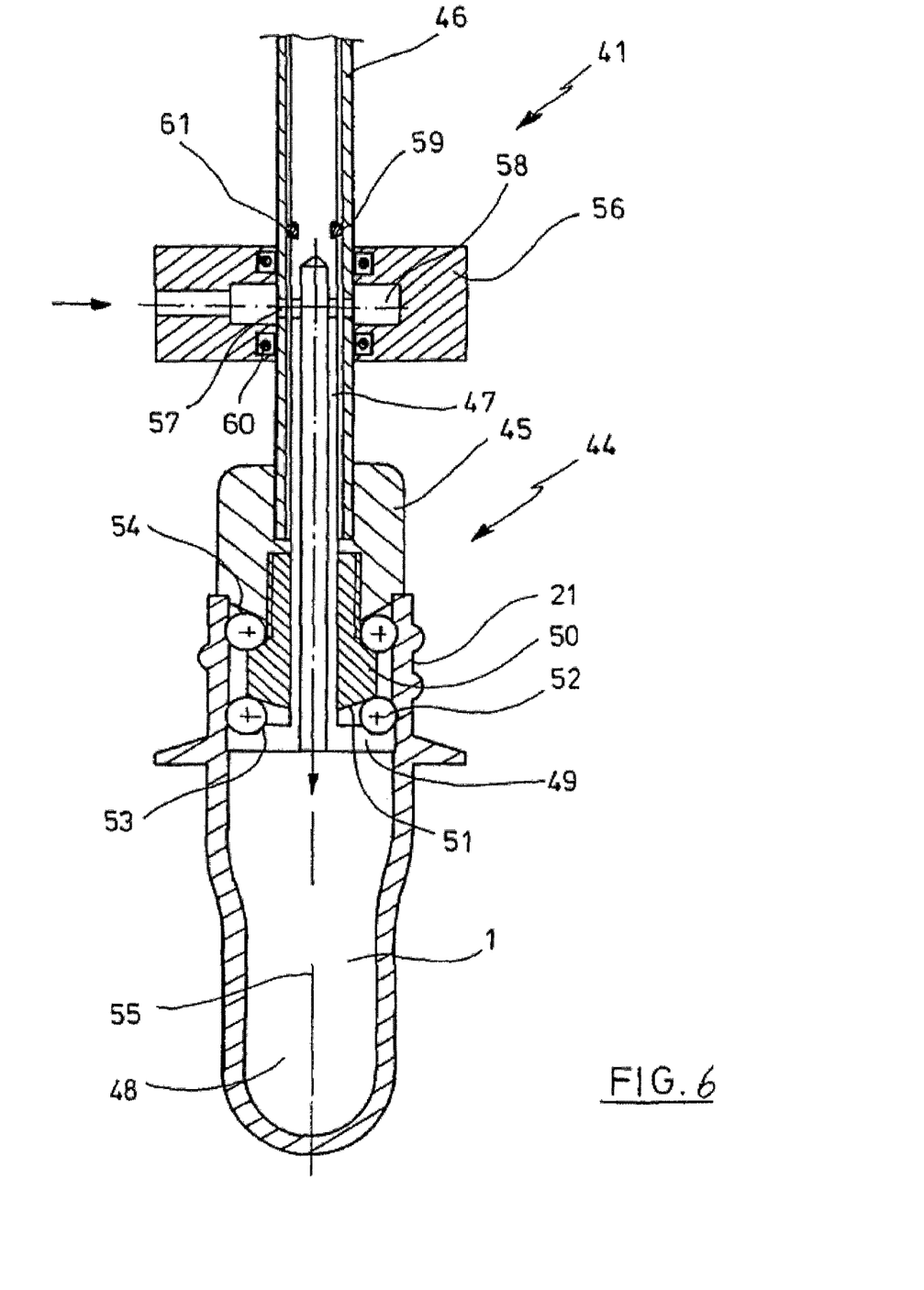
FIG. 6 shows a longitudinal section through an applicator for the sterilization agent, that is introduced into a mouth area of the parison.

FIG. 6 shows an area of the sterilization device (41) that is introduced with an applicator (44) into the mouth section (21) of the parison (1). The applicator (44) comprises a base element (45) carried by a positioning element (46). In the exemplary embodiment shown the positioning element (46) is constructed like a tube and an adjusting element (47) extends through the positioning element (46). The adjusting element (47) empties in the area of its extension facing an inner space (48) of the parison (1) into a tensioning element (49).

A wedge element (50) is arranged between the tensioning element (49) and the base element (45) which wedge element comprises at least one wedge surface (51) for loading at least one clamping element (52). The clamping element (52) is constructed to be rounded. A spherical design of the clamping element (52) is preferably present. The using of a ceramic material consisting of PEEK or a metal coated with a ceramic material is provided, for example, as material for the clamping element (52).

The tensioning element (49) comprises at least one wedge surface (53) in the area of its extension facing the wedge element (50). The base element (45) is also provided with at least one wedge surface (54) in the area of its extension facing the wedge element (50).

Therefore, in the exemplary embodiment shown at least two clamping elements (52) are positioned in the direction of a longitudinal axis (55) of the positioning element (46) in series and at a distance relative to each other. However, this is optional and not obligatorily necessary. Also, at least two clamping elements (52) are arranged in a circumferential direction of the clamping element (50) at a distance relative to each other. Preferably at least three clamping elements (52) are used that are spaced equidistantly relative to each other in the circumferential direction.

Figure 7:
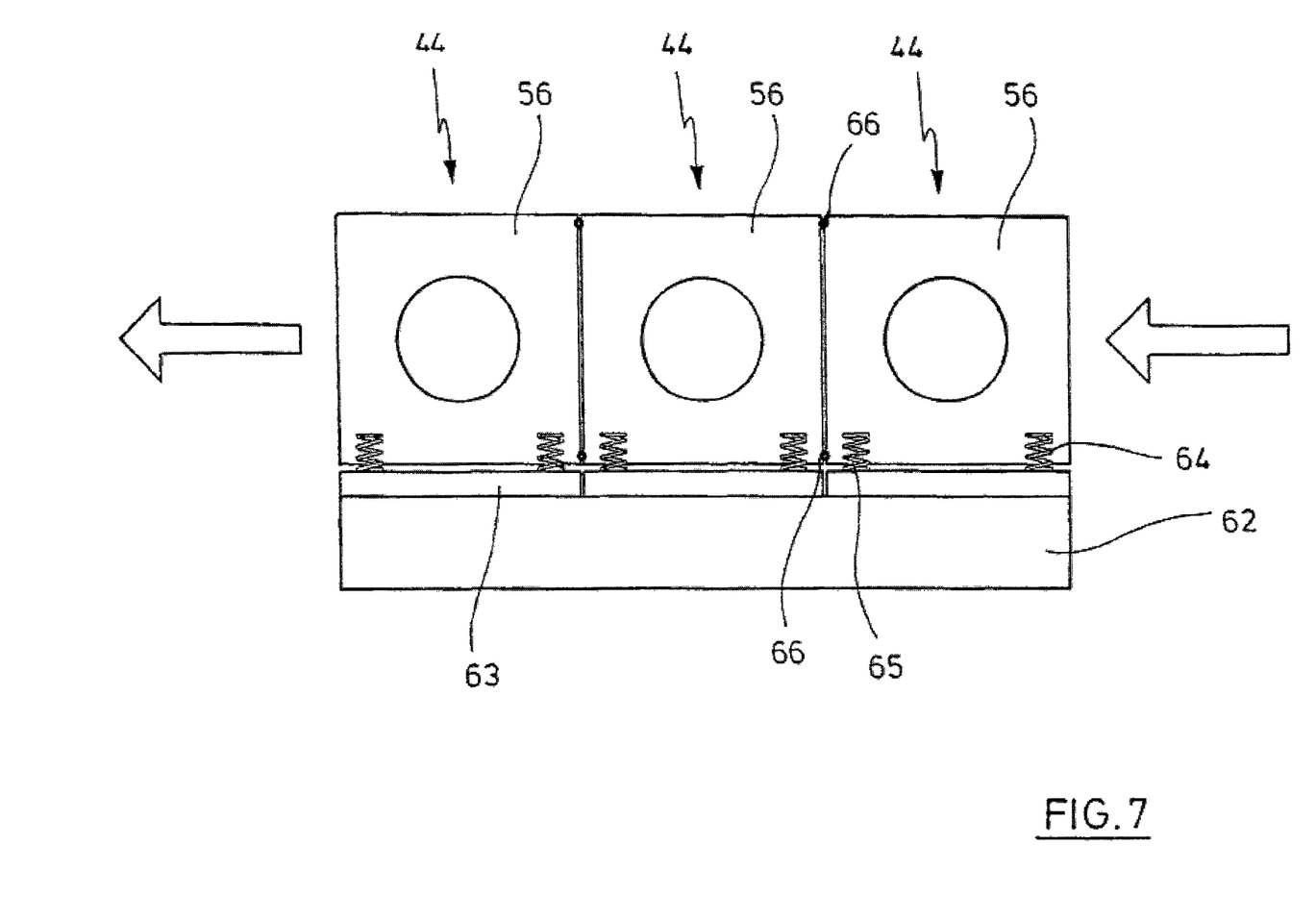
FIG. 7 shows a schematic top view onto applicators on which press-on elements are resiliently supported that are guided past a supply conduit.

For an introduction of the applicator (44) into the mouth section (21) or for a removal of the applicator (44) from the area of the mouth section (21) the distance between the tension element (49) and the base element (45) is enlarged by a positioning of the adjusting element (47) relative to the positioning in FIG. 7. The clamping elements (52) can travel as a result thereof in the direction of the adjusting element (47) further into receiving pockets limited by wedge surfaces (51, 52) or wedge surfaces (51, 54) and free the parison (1) relative to the applicator (44). Inversely, the clamping elements (52) are positioned upon a reduction of the distance between the tensioning element (49) and the base element (45) along the wedge surfaces (51, 53, 54) in the direction of the mouth section (21) of the parison (1) and as a consequence carry out a clamping procedure.

After a positioning of the applicator (44) in the area of the mouth section (41) sterilization agent is conducted into the area of the applicator (44) using a supply device (56). In the exemplary embodiment shown the tubular positioning element (46) has at least one outside recess (57) that empties into a supply space (58) of the supply device (56). The supply space (58) is sealed off by seals (59, 60) against the surroundings. The seals (59, 60) can be constructed, for example, as O-rings that surround the positioning element (46) on the outside.

A seal (61) is used in order to seal the adjusting element (47) relative to the positioning element (46). This seal (41) can also be constructed as an O-ring that is inserted into an outside, groove-shaped recess of the adjusting element (47).

In order to carry out a sterilization procedure the sterilization agent is introduced through the supply device (56) and the positioning element (46) into the parison (1). In the exemplary embodiment shown even the adjusting element (47) is constructed hollow at least in areas so that the supplying of the sterilization agent takes place through the hollow area of the adjusting element (47). As a result, a central introduction into the parison (1) can take place in the direction of the longitudinal axis (55).

A draining off of the sterilization agent from the inner space (48) can take place, for example, through conduits or grooves in the area of the applicator (44). In the simplest case a draining off takes place by suitable grooves past the clamping elements (52) in the direction of the surroundings.

The sterilization agent is preferably introduced in a gaseous state into the inner space (48). In particular, a temperature of the sterilization agent above 100° C. is provided. The parison (1) preferably has a temperature above 80° C. during the execution of the sterilization procedure in the area of its inner surface to be sterilized. The use of hydrogen peroxide is provided in particular regarding the sterilization agent.

According to the exemplary embodiment in FIG. 6 the supply device (56) is constructed as part of the applicator (44) and is transported in common with it.

FIG. 7 shows an embodiment in which a supply element (62) is arranged in a horizontal direction adjacent to a plurality of applicators (44) and supply devices (56) of the applicators (44). According to the exemplary embodiment shown the supply element (62) is positioned stationarily in the blow-molding machine. Press-on elements (63) are resiliently tensioned between the supply element (62) and the applicators (44) and the supply devices (56). A support of each of the press-on elements (63) is shown, each on four springs (64, 65), of which two springs (64, 65) are visible in the view. As a result of the resilient support the press-on element (63) can assume a plurality of different angular positions.

The exemplary embodiment presented shows the resilient support of the press-on elements (63) on the applicators (44) and on the supply devices (56). The press-on elements (63) are pressed here against the supply element (62). It is basically also possible to perform the resilient support relative to the supply element (62) and to guide the press-on elements (63) as a consequence resiliently tightened against the applicators (44) and the supply devices (56).

In order to avoid an uncontrolled exiting of a sterilization agent the applicators (44) and the supply devices (56) are sealed relative to each other, for example, using seals (66).

Figure 8:
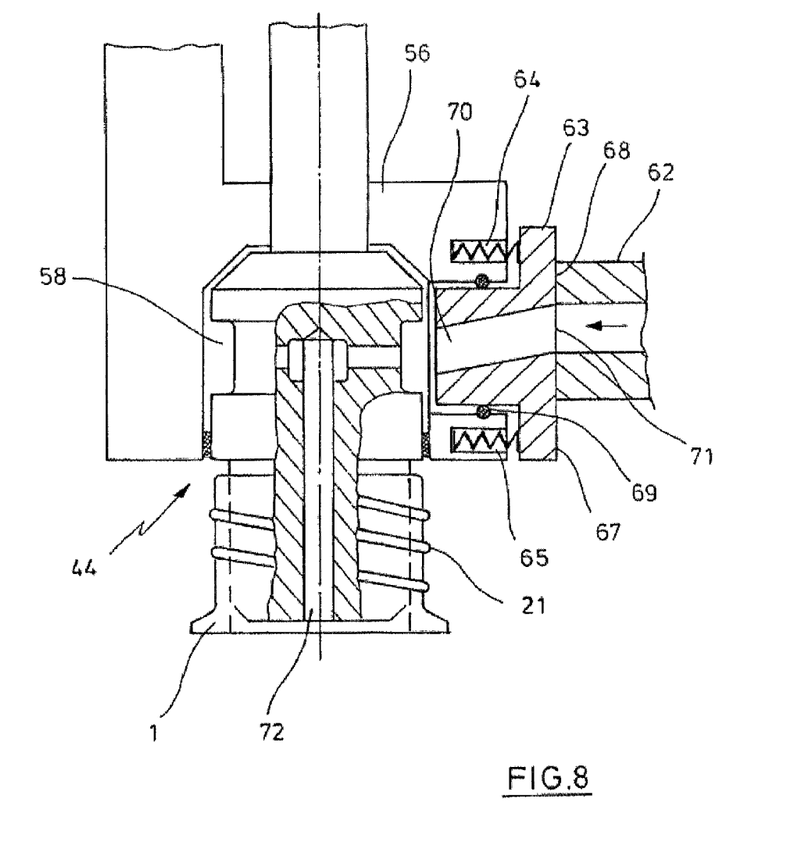
FIG. 8 shows a longitudinal section through an applicator with resiliently supported press-on element.

FIG. 8 shows a vertical section through an embodiment modified in comparison to FIG. 6.

It can be recognized that in this exemplary embodiment the press-on element (63) is resiliently supported on the supply device (56). The press-on element (63) is guided with a contact surface (67) against a surface (68) of the supply element (62). It was provided in particular that there would be no use of special seals in the transition area from the contact surface (67) to the surface (68). A seal can be achieved, for example, in that one of the structural elements (62, 63) is constructed of metal at least in the area of the surfaces facing one another and that the other structural element is constructed from a plastic. For example, the use of PTFE is provided. It proved to be advantageous, considering the effects of wear, to construct the press-on element (63) from metal and to construct the area of the supply element (62) facing the press-on element (63) from plastic.

A sealing of the press-on element (63) relative to the supply device (56) takes place using a seal (69). On the one hand, the seal (69) establishes the required sealing and in addition the movability of the press-on element (63) relative to the supply device (56) is allowed.

It can be recognized from FIG. 8 that a through conduit (70) of the press-on element (63) is positioned in such a manner that the through conduit (70) communicates with an outlet opening (71) of the supply element (52). The through conduit (70) is then connected via the supply space (58) of the supply device (56) to a longitudinal conduit (72) of the applicator (44) through which the sterilization agent is introduced into the inner space of the parison (1).

Figure 9:
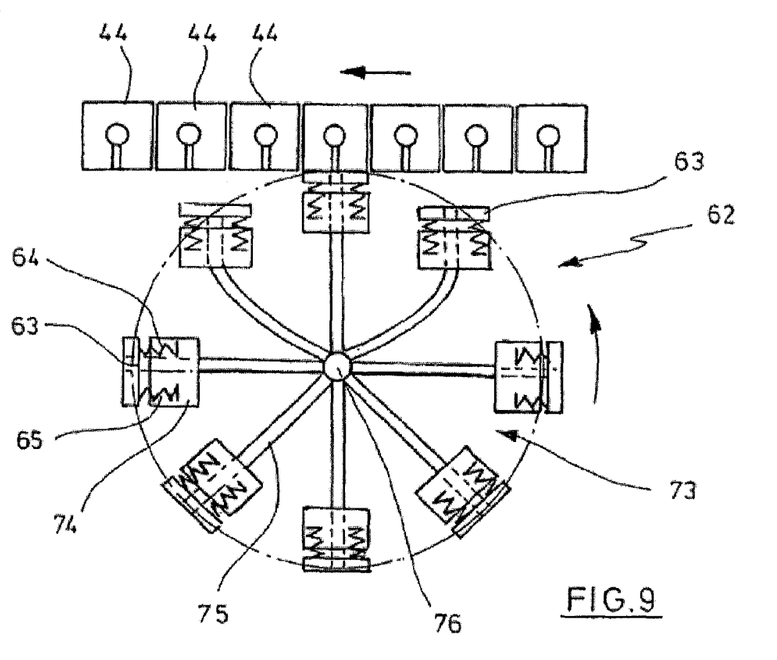
FIG. 9 shows a schematic view of applicators transported in a row that are loaded along their transport path by press-on elements arranged on a rotating wheel.

According to an alternate embodiment shown in FIG. 9 the supply element (62) is movably arranged in the blow-molding machine and is moved synchronously to the applicator (44) at least during the time of a transfer of the sterilization agent from the supply element (62) to the applicator (44). This avoids friction between the press-on element (63) and the corresponding structural element. The supply element (62) can be constructed to this end, for example, as a rotating wheel (73) that comprises a suitable number of dispensing elements (74) on its circumference.

According to the exemplary embodiment shown, in distinction to the embodiment in FIG. 7 the resiliently supported press-on elements (63) are positioned in the area of the supply element (62). Each of the dispensing elements (74) is concretely provided with a resiliently supported press-on element (63). The individual dispensing elements (74) are connected via connection lines (75) to a central distributor (76) for the sterilization agent. The connection lines (75) can be constructed, for example, from a flexible material in order to support a movable arrangement of the dispensing elements (74) on the wheel (73).

Figure 10:
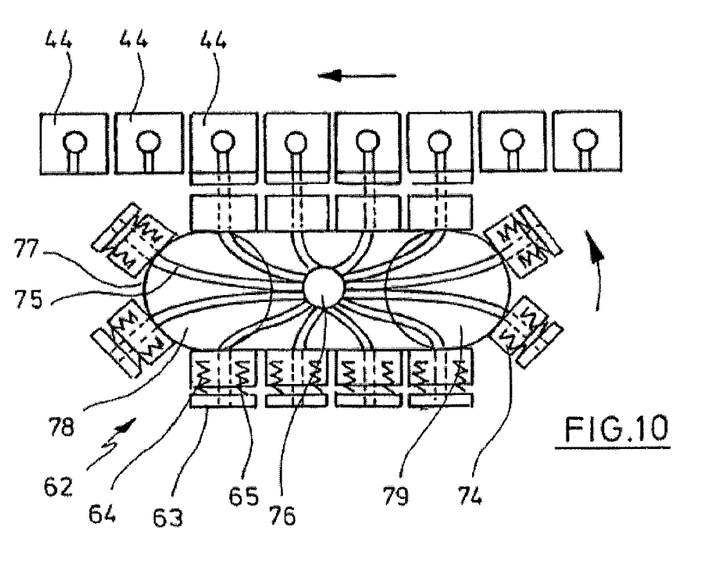
FIG. 10 shows an embodiment modified in comparison to FIG. 9 in which the press-on elements are arranged on a chain transported in a rotary manner.

According to another alternate embodiment shown in FIG. 10, instead of a rotating wheel (73) a rotating chain (77)

or comparable articulated arrangements can be used. The chain (77) is guided in the exemplary embodiment shown over two deflection wheels (78, 79).

The chain (77) runs in sections substantially parallel to the transport path of the applicators (44). As a result, a well-sealed contact is ensured between the press-on elements (63) and the particular corresponding structural elements.

Even when using supplying element (62) that are moved entirely or partially in a rotating manner it is possible to position the press-on element (63) selectively in the area of the supply element or in the area of the applicator (44) or of the supply device (56).

In particular, it is provided in an arrangement of the dispensing elements (74) in the area of a rotating wheel (73) that the dispensing elements (74) are positioned in a cam-controlled manner in such a manner that a movement takes place at least in sections not only synchronously but also parallel to the applicators (44).

The invention claimed is:

1. A device for sterilizing thermoplastic parisons configured for conversion into containers using a blow-molding machine, the device comprising a supply device for introducing a sterilization agent into an inner space of the parisons, wherein the supply device comprises:
   at least one applicator that is configured to be transported together with at least one of the parisons in at least a section of the blow-molding machine in which sterilization of the parisons takes place; and
   a supply element for supplying the sterilization agent, wherein the supply element is not configured to be transported together with at least one of the parisons, but is configured to engage the at least one applicator along a transport path of the at least one applicator in the section of the blow-molding machine in which the sterilization of parisons takes place;
   wherein the supply element has at least one discharge opening facing the at least one applicator,
   wherein at least one press-on element is arranged between the at least one applicator and the supply element, and
   wherein the at least one press-on element is resiliently mounted on one of the at least one applicator and the supply element.

2. The device according to claim 1, wherein the at least one applicator is constructed as part of a carrier element for the parisons.

3. The device according to claim 1, comprising at least two applicators, which are sealed against each other.

4. The device according to claim 3, wherein the at least two applicators are sealed against each other via a circumferential seal.

5. The device according to claim 1, wherein the at least one press-on element is resiliently mounted on the at least one applicator.

6. The device according to claim 1, wherein the at least one press-on element is resiliently mounted on the supply element.

7. The device according to claim 6, wherein the supply element is configured such that it does not move parallel to the transport path in the section of the blow-molding machine in which the sterilization of parisons takes place.

8. The device according to claim 6, wherein the supply element is movably arranged in the section of the blow-molding machine in which sterilization of the parisons takes place.

9. The device according to claim 8, wherein the supply element comprises dispensing elements arranged on a rotating wheel.

10. The device according to claim 8, wherein the supply element comprises dispensing elements arranged on a rotating chain.

11. The device according to claim 9, wherein at least one of the dispensing elements is guided parallel to the transport path of the at least one applicator at least in the section of the blow-molding machine in which sterilization of the parisons takes place.

12. The device according to claim 1, wherein the supply device is arranged in a heating section of the blow-molding machine where the parisons are converted into containers by blowing.

13. The device according to claim 10, wherein at least one of the dispensing elements is guided parallel to the transport path of the at least one applicator at least in the section of the blow-molding machine in which sterilization of the parisons takes place.

* * * * *